United States Patent [19]

Wolff et al.

[11] Patent Number: 5,050,616

[45] Date of Patent: Sep. 24, 1991

[54] UNIVERSAL COLLECTOR FOR SUBMANDIBULAR-SUBLINGUAL SALIVA

[75] Inventors: Andy Wolff, Raanana, Israel; Ronald L. Davis, Fort Washington, Md.

[73] Assignee: The United States of America as represented by the Secretary of the Department of Health and Human Services, Washington, D.C.

[21] Appl. No.: 493,538

[22] Filed: Mar. 14, 1990

[51] Int. Cl.⁵ .............................................. A61B 5/00
[52] U.S. Cl. ..................................... 128/760; 604/319
[58] Field of Search ................. 128/760, 768; 604/28, 604/35, 317, 319

[56] References Cited

U.S. PATENT DOCUMENTS

| | | | |
|---|---|---|---|
| 4,334,538 | 6/1982 | Juhn | 128/760 |
| 4,376,439 | 3/1983 | Lauterjung | 128/760 |
| 4,397,643 | 8/1983 | Rygiel | 604/317 |
| 4,402,687 | 9/1983 | Denty et al. | 604/319 |
| 4,455,140 | 6/1984 | Joslin | 128/760 |
| 4,460,361 | 7/1984 | Nichols | 604/319 |
| 4,564,359 | 1/1986 | Ruhland | 604/319 |
| 4,870,975 | 10/1989 | Cronk et al. | 128/760 |
| 4,950,247 | 8/1990 | Rosenblatt | 604/319 |
| 4,957,492 | 9/1990 | McVay | 128/760 |

Primary Examiner—Max Hindenburg
Attorney, Agent, or Firm—Lowe, Price, LeBlanc & Becker

[57] ABSTRACT

A fluid sampling device for sampling and collecting biological fluids from membrane bounded areas of a subject includes a buffering chamber to which a vacuum is applied, a sampling tube connector, a storage tube connector and a vent. In operation the vent is closed to apply the vacuum to a sampling tube connected to the sample tube connector to draw a sample into the buffering chamber. The drawn fluid flows, under gravitational force into a storage tube attached to the storage tube connector. The device is particularly useful for sampling and collecting submandibular and sublingual saliva.

19 Claims, 2 Drawing Sheets

UNIVERSAL COLLECTOR FOR SUBMANDIBULAR-SUBLINGUAL SALIVA

TECHNICAL FIELD

Present invention relates to an apparatus and method for sampling small volumes of fluid from areas bounded by a membrane. In particular, the present invention relates to an apparatus and method for sampling saliva from selective, discrete portions of a subjects mouth.

BACKGROUND ART

Saliva collection is a procedure with increasing clinical importance. It is a non-invasive means to assess the activity of a variety of diseases and the level of certain drugs and hormones (Ferguson, "Current Diagnostic Uses of Saliva," *J. Dent. Res.* 66:420-424(1987)). Whole saliva is a mixture of fluids secreted by the salivary glands, but also contains fluids, debris and cells not originating in the salivary glands. Therefore, the analysis of the individual gland saliva is usually a more reliable procedure for diagnostic purposes then the analysis of whole saliva (Fox et al, "Xerostomia: Evaluation of a Symptom with Increasing Significance," *J. Am. Dent. Assoc.* 110:519-525(1985)).

Saliva can be collected in a resting or a unstimulated state, reflecting secretion during most of the day, or in a stimulated condition, emulating salivary gland stimulation by food. Depending on the degree of stimulation, submandibular-sublingual (SM/SL) glands contribute between about 30 and 60% of the total volume of saliva (Schneyer, "Source of Resting Total Mixed Saliva of Man," *J. Appl. Physiol.* 9:79-81(1956); Mason et al, "Salivary Glands in Health and Disease," London; W. B. Saunders, pp. 37-39(1975)).

While saliva secreted from the parotid glands is relatively easy to collect using established methods (Carlson et al, "The Relationship of Ptyalin Concentration to the Diet and to the Rate of Secretion of Saliva", *Am. J. Physol.* 26:169-177(1910)). There is no universally accepted method for the collection of secretions from SM/SL glands. This difficulty is best illustrated by the fact that most saliva collections for research purposes reported in the scientific literature are limited to parotid or whole saliva.

One way of collecting submandibular or sublingual saliva is to cannulate the excretory ducts of the respective glands (Mandel, "Sialochemistry in Diseases and Clinical Situations Affecting Salivary Glands," *Crit. Rev. Clin. Lab. Sic.* 12:321-366(1980)). However this procedure is invasive and painful, and requires special skills.

One alternative to collecting saliva by cannulation is to use a collector placed externally to the ducts' openings. Schneyer, "Method for the Collection of Separate Submaxillary and Sublingual Salivas in Man," *J. Dent. Res.* 34:257-261(1955), proposed a custom made collector of an acrylic material. Others including Henriques et al, "A Modified Method for the Collection Submaxillary and Sublingual Saliva," *Oral Surg.* 9:1124-1129(1961); Stephen et al, "A Modified Appliance for the Collection of Human Submandibular and Sublingual Salivas" *Arch. Oral Biol.* 23:835-837(1978); and Parr et al, "A Modified Segregator for Collection of Human Submandibular and Sublingual Saliva," *Arch. Oral Biol.* 29:69-71(1984) made several modifications to custom made acrylic collectors. A major disadvantage associated with such custom made collectors is the amount of time and effort needed to construct each collector for individual subject use.

Although custom made devices made of impression materials (Morse et al, "Stress, Meditation and Saliva: A Study of Separate Salivary Gland Secretions in Endodontic Patients," *J. Oral Med.* 38:150-160(1983); McCarthy et al, "A Method for Collection of Submandibular Saliva from Dentate Patients," *Br. Dent. J.* 162:148-150(1987) and Oliveby et al, "Studies on Fluoride Concentrations in Human Submandibular/Sublingual Saliva and their Relation to Flow Rate and Plasma Fluoride Levels," *J. Dent. Res.* 68:146-149(1989) shortened the time and reduce the number of steps involved in the construction of such devices, a significant time is still required to construct these collectors. Further drawbacks to such appliances include their lack of standarization when sampling different subjects, especially adults and children.

Universal appliances have been proposed. However, most universal appliances require individual adaptation with impression material (Battistone et al, "The Free Amino Acid Composition of Human Saliva," *Arch. Oral Biol.* 3:161-170(1961); Block et al "A Method of Submaxillary Saliva Collection without Cannulization," *N.Y. State Dent. J.* 28:1160-118(1962); Marder et al, "A New Stabilizing Device for the More Accurate Collection of Submaxillary Saliva," *N.Y. State Dent. J.* 31:301-303(1965) and Coudert et al, "A New Appliance for the Collection of Human Submandibular Saliva," *Arch. Oral Biol.* 31:411-413(1986)).

An appliance designed by Truelove et al, "Simplified Method for Collection of Pure Submandibular Saliva in Large Volumes," *J. Dent. Res.* 46:1400-1403(1967) requires that certain tongue movements and swallowing patterns be performed by the subjects. This necessary method of use poses a difficulty in dealing with children and handicapped persons. In addition, some difficulties may arise in edentulous patients.

Systems similar to those described above also share a disadvantage in their relative bulk. When positioned within a patient's mouth, the size of these devices often distort measurements of unstimulated saliva flow, which has to be collected under resting conditions, with the subject feeling as comfortable as possible and minimizing the subjects perception of foreign bodies in their mouth.

While the use of a micropipette suction device has proven generally successful (Tylenda et al, "Evaluation of Submandibular Salivary Flow Rate in Different Age Groups" *J. Dent. Res.* 67:1225-1228(1988)), associated drawbacks include frequent loss of part of the saliva sample into the suction device and the safety risk produced by the use of a glass micropipette. One particular system which utilizes micropipettes has been found to cause difficulty in use during continuing gustatory stimulation (Pedersen et al, "Age-dependent Decreases in Human Submandibular Gland Flow Rates Under Resting and Post-Stimulation Conditions," *J. Dent. Res.* 64:822-825(1985)).

The present invention is an improvement over prior art saliva sampling devices which provides for easy sampling and high reliability and standardization among subjects.

DISCLOSURE OF THE INVENTION

It is accordingly one object of the present invention to provide a fluid sampling device which can be used to collect small samples of fluids in areas bounded by membranes.

Another object of the present invention is to provide for a device for sampling and collecting submandibular and sublingual salivas from a subject's mouth.

A further object of the present invention is to provide for a submandibular and sublingual saliva sampling and collecting device which is simple to use and highly reliable.

Still further object of the present invention is to provide a method for sampling and collecting small volumes of fluid from areas bounded by membranes.

An even further object of the present invention is to provide a method for sampling and collecting submandibular and sublingual salivas from a subject's mouth.

BRIEF DESCRIPTION OF DRAWINGS

The present invention will now be described with reference to the annexed drawings, which were given by way of non-limiting examples only in which.

BEST MODE FOR CARRYING OUT THE INVENTION

The sampling device of the present invention is designed to both sample and collect liquid from areas of animal and human subjects bounded by membranes. In particular, the sampling device is designed to sample and collect fluids such as saliva which may contain bubbles. In this regard, the sampling device of the present invention is particularly designed so that any bubbles contained in the sampled fluid are caused to rupture in a buffering chamber so as to insure a full recovery of the collected sample in an appropriate storage tube.

The sampling device of the present invention was designed particularly to sample and collect saliva from a subject's mouth. However, the present sampling device, is not limited to use in saliva sampling but, can be effectively used to sample and collect any fluid from areas bounded by membranes. Thus, the present device has been found to be particularly advantageous to sample fluids from the pleural cavity, peritoneum, intracranially and similar membrane bounded areas.

Since the sampling device of the present invention is utilized to sample fluids for clinical evaluation the overall device itself, or at least reusable portions thereof, should be made of an autoclavable material so that the device can be sterilized and reused. In a particular embodiment, the device of the present invention is made out of a plastic material such as polycarbonate. If the device is designed to be discarded after use, it is sufficient to make the device out of any inert material which will not react with the sample fluid so as to affect any desired clinical evaluation of the sampled fluid. In the instance wherein the device is made to be discarded after use, it is obviously unnecessary to make the device out of an autoclavable material, and thus any suitable inert plastic material may be utilized.

The sampling device of the present invention is designed to be used in a collecting system which includes a collecting tube which is attachable to the sampling device, a buffering chamber which is centrally located within the interior of the sampling device, a storage tube which is attachable to the sampling device and a suction device or vacuum device which is connected to the sampling device.

Figure 1:
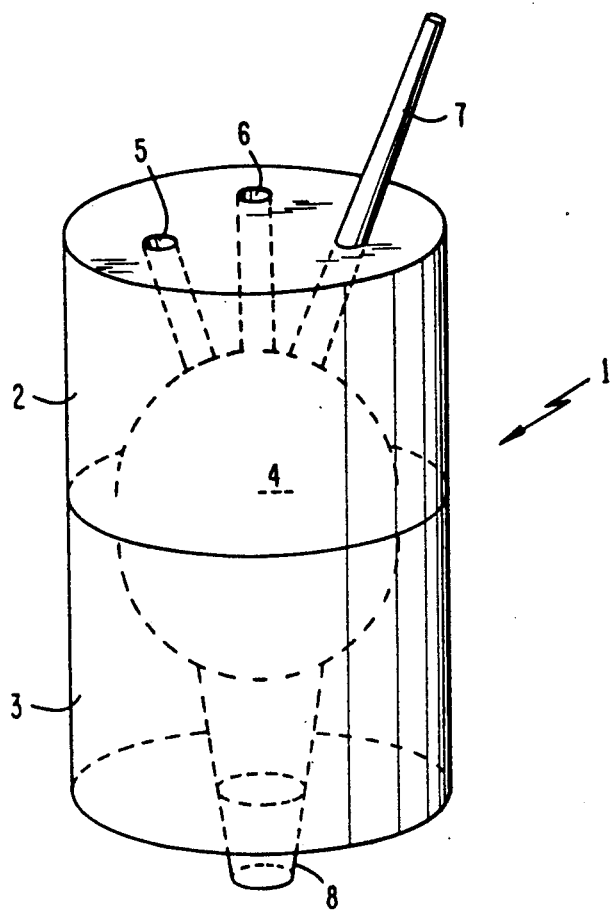
FIG. 1 is an illustration showing the details of the buffering chamber according to a preferred embodiment of the present invention.

FIG. 1 illustrates one embodiment of the sampling of the present invention. As seen in FIG. 1 sampling device 1 includes two chamber portion 2 and 3 which are connectable together to form a sampling chamber having an interior buffering chamber 4. The sample chamber is made of portions 2 and 3 which are sealingly connectable together by means of suitable thread connections or pressure connections, or the like so that the chamber may be opened by separating the two chamber portions for cleaning the interior of the device. If the device is designed to be disposable, it is not necessary that the sampling device be openable and thus chamber portions 2 and 3 may be permanently attached together or the sampling device may be made from one chamber element.

As illustrated in FIG. 1, sampling chamber has two through-holes located in an upper portion thereof, 5 and 6, and a tube connecting means 7 which is also in fluid communication with the internal buffering chamber. Through-hole 5, as will be discussed in detail below, is designed to receive a collecting tubing therein. Each of the through-holes 5 and 6 and the tube connecting number 7 include through-bores within the upper portion of the sampling chamber whose central axes intersect within or below the internal buffering chamber. In this regard, the bores of at least through-hole 5 and 6 are inclined from the central axis of the buffering chamber as illustrated in FIG. 1. In a lower portion of the sampling chamber as illustrated in FIG. 1, a storage tube attachment means 8, depends from the lower portion of the sampling chamber and is in fluid communication with the interior buffering chamber.

Although the storage tube connection means is illustrated as a projecting nipple having an inclined or tapered outer surface, any suitable means may be utilized to connect a storage tube such as snap-fit, screw threads, or the like. Similarly, tube connecting means 7 in a preferred embodiment includes a projecting member whose outer surface is tapered so that a tubing member can be slid on the outer surface thereof. However, other suitable means may be utilized for connecting a tube member to the bore of tube connecting means 7, including a pressure fit, screw thread, or the like.

As illustrated in FIG. 1, the interior buffering chamber 4 has a spherical shape in a preferred embodiment. This shape allows fluid entering through-hole 5 to collect at a lower portion in the buffering chamber and pass through storage tube connection means 8 and into an attached storage tube (not shown). In this manner it is noted that other tapered interior surface shapes may be utilized for the buffering chamber such as conical, pyramidal, or other similar type of shapes which allow the fluid to flow downwardly into the storage tube under the influence of gravitational forces.

The outer surface of the sampling chamber is illustrated in FIG. 1 as being cylindrical. However, other shapes may be equally suitable for specific applications such as spherical or other shapes for hand-held operation. In this regard, the outer shape of the sampling chamber may be made to conform in part or in whole to a operator's hand for ease of use.

Figure 2:
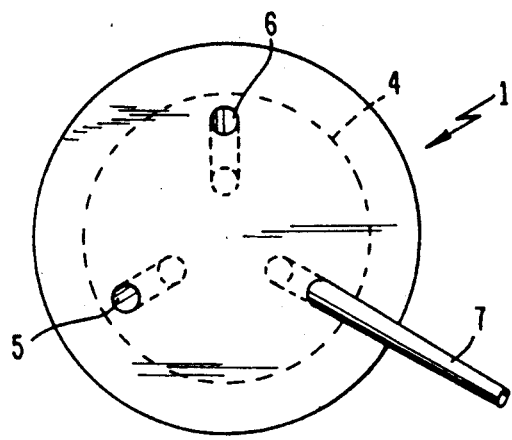
FIG. 2 is an illustration showing the upper surface of the buffering chamber of FIG. 1.

As mentioned above, at least the bores of through-holes 5 and 6 should be inclined from the central axis of the sampling chamber. This alignment is illustrated in FIG. 2 in which the bores of each through-hole 5 and 6 and tube connecting means 7 are illustrated as being inclined inwardly from the upper surface of the sample chamber in relation to the central axis of the sample chamber.

Figure 3:
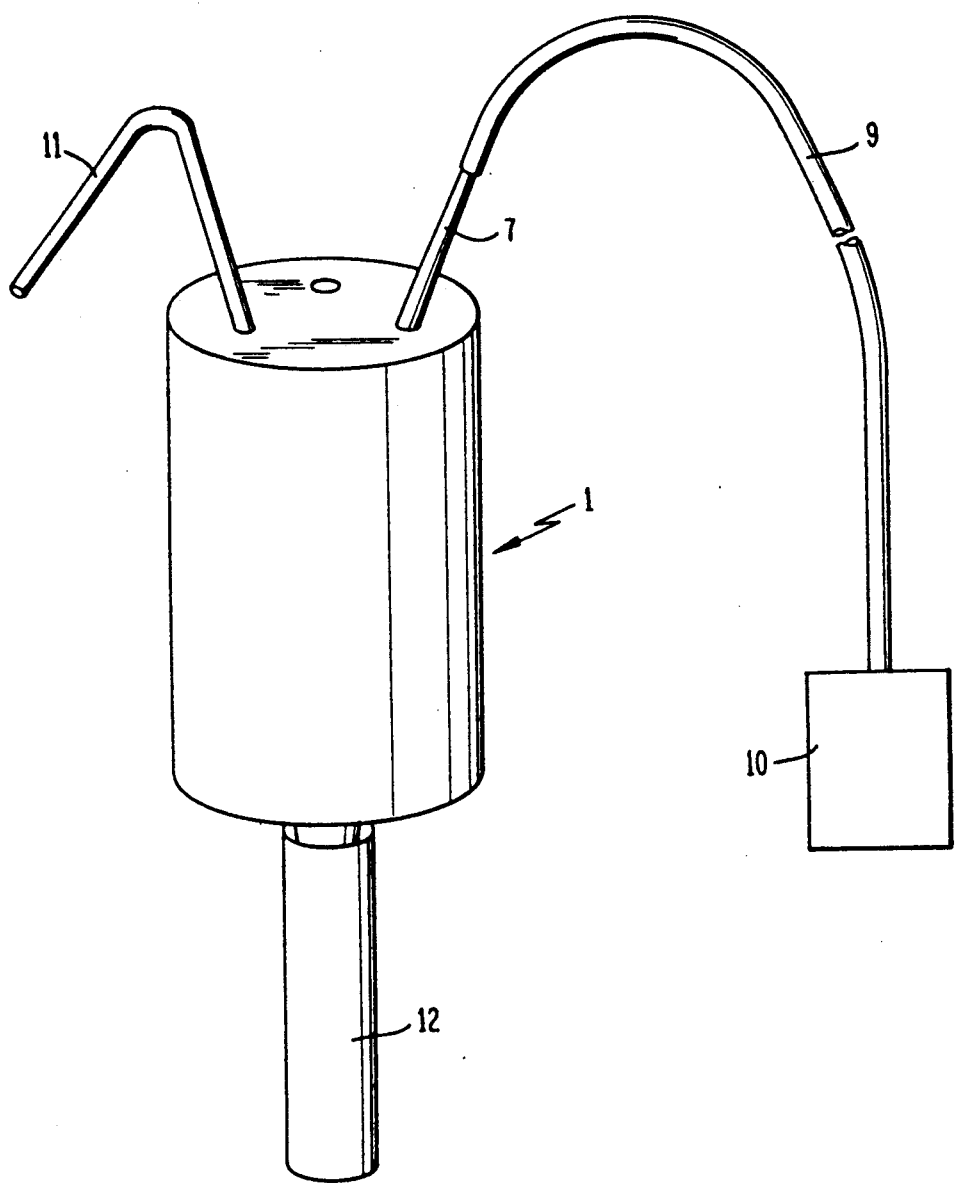
FIG. 3 is a partially schematic illustration of the overall apparatus used to sample fluids according to one embodiment of the present invention.

FIG. 3 illustrates the overall fluid collecting system of the present invention. In FIG. 3 sampling device 1 is connected by means of the tube connecting means 7 to a vacuum source 10 by means of a suitable tube 9. A sample collecting tube 11 is illustrated as being inserted into through-hole 5 and a sample storage tube 12 is illustrated as being connected to storage tube connecting means 8 as illustrated.

In operation, vacuum source 10 applies a slight vacuum to the interior buffering chamber which is vented by means of through-hole 6. To sample fluid, an operator places his thumb or finger or otherwise seals the opening of through-hole 6 so that the vacuum within buffering chamber 4 is applied to collecting tube 11 located in through-hole 5. As the sample is drawn through collecting tube 11 by means of the vacuum, fluid entering through-hole 5 flows down the interior tapered surfaces of the buffering chamber and collects in attached storage tube 12. The sampling is controlled by the operators opening and closing of through hole 6 to thereby control the vacuum applied to sampling tube 11.

In a more preferred manner of operation the sampling tube is positioned in through-hole 5 and extends through the buffering chamber to terminate within or below storage tube connecting means 8. When the vacuum is applied to the sampling tube as positioned in this embodiment, the sampled fluid is delivered directly onto the interior surface of the storage tube.

The sampling device of the present invention may be sized according to the particular fluid and volume thereof to be sampled. For instance, when designed for sampling submandibular and sublingual saliva, the size of the sampling device should be minimized so as to be more easily manipulated to sample fluids from a subject's mouth. In other instances, when the sampling volume may be larger than that normally sampled by saliva glands, a larger collecting device may be required.

In a particular embodiment of the present sampling device which was designed to sample and collect submandibular and sublingual saliva, the sample collecting tube had an outer diameter of ⅛", and an inner diameter of 1/16". The sample collecting tube was made of a cellulose acetate butyrate tubing, which was autoclavable and cold formable. By being cold formable, it was possible to easily configure the shape of the collecting tube as required for intraoral use. Alternative storage tubes connected to the device included a 5 mL polystyrene tube and a 1.5 mL centrifuge tube. The vacuum source was connected to the device by means of a length of tygon tubing having an outer diameter of 1/16" and an inner diameter of 1/32". The length of this tubing was long enough to allow for easy access to the mouth of a subject whose sample was to be collected.

All the parts described above were connected to the buffering chamber which was constructed of polycarbonate, an autoclavable material. The sampling device utilized for submandibular and sublingual saliva collection was about 4 cm long and about 2.5 cm wide.

The main function of the buffering chamber was to avoid suctioning of saliva into the vacuum source, thereby allowing full recovery of collected sample in the storage tube. The buffering chamber provided sufficient space between the through-holes and tube connecting means so that bubbles in the sampled fluid would expand and break at an upper interior surface within the buffering chamber and the fluid would flow downward to be received in the storage tube. In the above-discussed embodiment wherein the sampling tube extends through the buffering chamber, any bubbles present in the sample fluid expand and break as they exit the sample tube or as they rise into the buffering chamber.

The following examples are presented to illustrate the features of the present invention which is not intended to be considered limited thereto.

EXAMPLE 1

In this example, four healthy individuals, ranging in age between 35 and 41 years participated as operators, and three of them as subjects. Each subject's SM/SL saliva was collected consecutively by three operators so that a total of nine saliva samples were obtained. After isolating SM/SL duct openings with four pieces of gauze (one over each parotid duct opening, one in the lower vestibulum and one behind the SM/SL ducts' openings), SM/SL saliva was collected while stimulating saliva secretion with a solution of 2% citric acid which was swabbed every 30 seconds on the antero-dorso-lateral surfaces of the tongue. The solution used for the last collection of each subject contained 10% bacterial plaque disclosing dye (Lorvic, St. Louis, Mo., U.S.A.). Fluid content of all parts of the collecting system, except the vacuum pump was determined gravimetrically for each collection. Absorbance at 900 nm of all saliva samples contained in the storing tubes was measured in a spectrophotometer (Gilford 260, Overlin, Ohio., U.S.A.). A Student's T test was used to compare absorbance values of the saliva samples obtained from collections with and without the disclosing dye. The results of this example are listed in table 1 below.

TABLE 1

| Salivary volume values of nine saliva collections in trial no. 1 (mean ± standard deviation) | |
|---|---|
| Total volume (mL) | 0.480 ± 0.258 |
| Percent of volume collected in: | |
| collecting tubing | 3.8 ± 2.9 |
| buffering chamber | 0.5 ± 0.4 |
| suction tubing | 0.0 |
| storing tube | 95.7 ± 3.0 |

EXAMPLE 2

Three individuals participated in this second trial. The Sm/Sl saliva of each was collected by the other two individuals using the same procedure as in Example 1 above except no dye was added in this trial. Salivary volumes were determined gravimetrically utilizing the fluid accumulated in the storing tube. Flows were expressed as mL/min/gland, where gland refers to both submandibular and sublingual glands of one side. The results of this example are given in Table 2 below.

TABLE 2

Salivary volume (mL) and flow (mL/min/gland) values of trial 2

| Col- | Subject | | | | | |
| --- | --- | --- | --- | --- | --- | --- |
|  | A | | B | | C | |
| lector | Volume | Flow | Volume | Flow | Volume | Flow |
| A | — | — | 1.224 | 0.204 | 2.821 | 0.470 |
| B | 4.207 | 1.052 | — | — | 3.216 | 0.536 |
| C | 4.155 | 1.039 | 1.075 | 0.179 | — | — |

The results of the above examples prove the reliability of the present collecting system. The mean absorbance value of saliva samples collected without the use of disclosing dye was $0.227 \pm 0.061$ and with the disclosing dye, $0.253 \pm 0.118$ ($P=0.66$). This data suggests that the salivary samples were not contaminated by the gustatory stimulant swabbed over the tongue. The isolation of the SM/SL duct openings from parotid duct openings is greater than from the tongue surface. Therefore, contamination by the parotid saliva was not likely. It is thus concluded that this system enables collection of relatively pure samples of SM/SL saliva.

The data shown in Table 1 above indicated that the system makes possible an almost full recovery of collected SM/SL saliva in the storing tube for measurements of flow and composition. Flow volumes obtained in Example 2 (Table 2) illustrate the high degree of reproducibility of the measurement that this system provides, even with the limitations of variations resulting from a complex biological system such as saliva secretion and from repeated collection by two different operators. The present invention provides a useful tool to facilitate more frequent use of SM/SL in future salivary research.

Although the invention has been described with reference to particular means, materials and embodiments, from the foregoing description, one skilled in the art can ascertain the essential characteristics of the present invention in various changes and modifications may be made to adapt the various uses and characteristics thereof without departing from the spirit and scope of the present invention as described in the claims which follow.

We claim:

1. A fluid sampling device comprising a chamber means having first and second opposed surfaces, said chamber means defining an interior space having inclined wall surfaces, two through-holes located in said first surface of said chamber means, wherein one of said through-holes is adapted to receive a sampling tube, a tube connecting means located on said first surface of said chamber means, and being in fluid communication with said interior space and a storage tube receiving means located on said second surface of said chamber means being in fluid communication with said interior space, said first surface comprising a substantially spherical surface.

2. A fluid sampling device according to claim 1, wherein said chamber means has an outer surface which defines a cylindrical shape.

3. A fluid sampling device according to claim 1, wherein said chamber means comprises two chamber portions which may be assembled together to form said chamber means.

4. A fluid sampling device according to claim 1, wherein said two through-holes and said tube connecting means comprise bores having central axes wherein said axes of at least said through-holes intersect below said first surface.

5. A fluid sampling device according to claim 1, wherein said tube connecting means comprises an extension having a tapered outer surface.

6. A fluid sampling device according to claim 1, wherein said storage tube receiving means comprises an extending nipple having tapered exterior surfaces.

7. A fluid sampling device according to claim 1, wherein said sampling device is made from an autoclavable plastic material.

8. A fluid sampling device according to claim 1, wherein said device is disposable.

9. A fluid sampling device according to claim 1 in combination with a sampling tube positioned in said through-hole adapted to receive said sampling tube and further in combination with a vacuum source connected to said tube connecting means.

10. A fluid sampling device according to claim 9, wherein said sampling tube is made from a cold formable material.

11. A fluid sampling device according to claim 1, wherein said chamber means is about 4 cm. long and about 2.5 cm. wide.

12. A method of sampling biological fluid from a subject which comprises:
applying a vacuum to a buffering chamber having an opening vent and a sampling tube connected thereto, said buffering chamber comprising a substantially spherical chamber;
closing said vent to apply the vacuum to said sampling tube;
contacting said sampling tube to an area containing fluid to be sampled so as to draw fluid through said sampling tube into said buffering chamber and;
collecting said drawn fluid into a storage tube attached to said buffering chamber as said fluid leaves the sampling tube.

13. A method according to claim 12, wherein said area containing said fluid is selected from the group consisting of the subject's mouth, pleural cavity, peritoneum and intracranially.

14. A method according to claim 13, wherein said area containing said fluid is the subject's mouth and the fluid is selected from the group consisting of submandibular saliva, sublingual saliva and mixtures thereof.

15. A method according to claim 12, wherein said fluid drawn into said buffering chamber contains bubbles which are allowed to expand and break so as to insure substantially total collection of the fluid sample.

16. A method according to claim 12, wherein said sampling tube is cold formable and is manually configured to conform to the area wherein said fluid is sampled.

17. A method according to claim 12, wherein said buffering chamber is autoclaved and utilized in further fluid sampling procedures.

18. A method according to claim 12, wherein said buffering chamber is disposable and discarded after said fluid sampling is completed.

19. A method according to claim 12, wherein said collecting tube comprises a centrifuge tube.

* * * * *